United States Patent [19]

Kakibayashi et al.

[11] Patent Number: 5,552,602
[45] Date of Patent: Sep. 3, 1996

[54] ELECTRON MICROSCOPE

[75] Inventors: Hiroshi Kakibayashi, Nagareyama; Yasuhiro Mitsui, Fuchu; Hideo Tadokoro, Nishitama-gun; Katsuhiro Kuroda, Hachiouji; Masanari Koguchi, Higashikurume; Kazutaka Tsuji, Hachiouji; Tatsuo Makishima, Katsushika-ku; Mikio Ichihashi, Kodaira; Shigeto Isakozawa, Hitachinaka, all of Japan

[73] Assignee: Hitachi, Ltd., Tokyo, Japan

[21] Appl. No.: 398,684

[22] Filed: Mar. 6, 1995

Related U.S. Application Data

[60] Continuation-in-part of Ser. No. 79,273, Jun. 21, 1993, abandoned, which is a division of Ser. No. 882,970, May 14, 1992, Pat. No. 5,278,408.

[30] Foreign Application Priority Data

May 15, 1991  [JP]  Japan ..................... 3-110126

[51] Int. Cl.$^6$ .................................. H01J 37/26
[52] U.S. Cl. .............................. 250/311; 250/397
[58] Field of Search ............................. 250/311, 397, 250/307, 306, 310

[56] References Cited

U.S. PATENT DOCUMENTS

| | | | |
|---|---|---|---|
| 4,680,469 | 7/1987 | Nomura et al. | 250/311 |
| 4,975,578 | 12/1990 | Tomimasu et al. | 250/397 |
| 5,278,408 | 1/1994 | Kakibayashi et al. | 250/311 |

OTHER PUBLICATIONS

*Ultramicroscopy*, "Filtered Dark–Field and Pure Z–Contrast: Two Novel Imaging Modes in a Scanning Transmission Electron Microscope", M. Haider, 1989, North–Holland, Amsterdam.

*Fiber Optically Coupled TV System*, Model 622SC.

Primary Examiner—Jack I. Berman
Assistant Examiner—Kiet T. Nguyen
Attorney, Agent, or Firm—Antonelli, Terry, Stout & Kraus

[57] ABSTRACT 3-dimensional observation on the atomic arrangement and atomic species in a thin-film specimen as well as conventional electron microscope observations is carried out at high speed and accuracy by an electron microscope which measures electrons emitted at high angle from the specimen. For that purpose, the present invention provides a scanning transmission electron microscope having an electron detection device comprising a scintillator converting electrons detected thereby to photons, a photoconductive-film converting photons from the scintillator detected thereby to c.a. 1000 times as many electron-hole pairs as these photons (i.d. avalanche multiplication), an electron gun emitting an electron beam toward the photoconductive-film to detect the holes generated therein, and electron deflector electrodes deflecting the electron beam on the photoconductive-film. Avalanche multiplication in the photoconductive-film amplifies the signal of these photons at so high signal-to-noise ratio that the electron microscope in this invention can detect such weak electrons as emitted at high angle from the specimen at high sensitivity and resolution. Therefore this invention enables a scanning transmission electron microscope to obtain for example 3-dimensional image of point defects and impurity elements existing in joint interfaces and contacts in a ULSI device rapidly and accurately.

28 Claims, 14 Drawing Sheets

| DETECTOR TYPE | FIRST QUANTUM EFFICIENCY | MULTIPLICATION FACTOR | RELATIVE SENSITIVITY | S/N |
|---|---|---|---|---|
| PHOTOMULTIPLIER | 0.2 | $10^5$ | HIGH | POOR |
| CONVENTIONAL PHOTO-CONDUCTION TYPE IMAGING DEVICE | 0.4 | 1 | LOW | GOOD |
| AVALANCHE-TYPE IMAGING DEVICE | 1.0 | $10^3$ | HIGH | GOOD |

ELECTRON BEAM SCANNING SHAPE ON PHOTO-CONDUCTIVE FILM SURFACE

HEAT TREATMENT
(450°C, 30 MINUTES)

BACK ETCHING OF Si
SINGLE CRYSTAL WAFER 74

ELECTRON MICROSCOPE

CROSS REFERENCE TO RELATED APPLICATIONS

This application is a continuation-in-part of application Ser. No. 08/079,273 filed on Jun. 21, 1993 now abandoned, which is a divisional of application Ser. No. 07/882,970 filed on May 14, 1992, now U.S. Pat. No. 5,278,408. The disclosure of application Ser. Nos. 08/079,273 and 07/882,970 are hereby incorporated by reference.

BACKGROUND OF THE INVENTION

The present invention relates to an electron microscope for the observation of point defects, impure atoms and their clusters which exist at joint interfaces and contacts in an integrated device formed into a layered structure such as a memory or fast-calculation device.

The present invention also relates to an electron detection instrument for an electron microscope, especially for the purpose described above. More particularly, it concerns an electron detection instrument for observing an electron microscope image corresponding to a specific atomic configuration or crystal structure of a specimen by way of measuring scattered, diffracted, refracted, or transmitted electrons through a specimen at a high sensitivity and a high signal-to-noise ratio in a desired range of detection angle.

As described in Proc. Mat. Res. Soc. Symp. Vol. 183 (Materials Research Society, San Francisco, 1990) p. 55, the conventional electron microscope can be used for inferring a 3-dimensional atomic arrangement from several electron microscope images observed from different directions. In addition, a technique for obtaining a 2-dimensional image of a 3-dimensional atomic structure is disclosed in Japanese Patent Laid-open No. 61-78041.

On the other hand, a prior electron detection instrument for an electron microscope is constructed as shown in FIG. 18, disclosed in the "Ultramicroscopy," 28, (1989), 240. In the figure, the electron detection instrument is placed in an STEM (scanning transmission electron microscope). The STEM comprises an electron gun 20, illumination lenses 21, electron deflector coils 22, and objective lenses 23. The electron detection instrument comprises an electron-photon converting scintillator 31, light guides 32, photomultipliers 33, and a monitor 34. There are provided two separate electron detection instruments for use of different detected electrons. One electron detection instrument is for observing a dark-field image only with electrons scattered at a high angle, having an annular scintillator 31a. The other electron detection instrument is for observing a bright-field image only with transmitted electrons at a low angle, having a circular scintillator 31b. In operation, the scintillator 31 detects electrons from the specimen, and then converts these electrons to photons. These photons are fed to the photomultiplier. A signal output of the photomultiplier 33 corresponds to intensity of the electrons. The output signal is synchronized with scanning the incident electron beam by a scanning circuit 25 before being brightness-modulated and displayed on the monitor 34. The monitor 34 shows an electron microscope image.

A prior imaging instrument for electron microscope is constructed as shown in FIG. 19, the instrument being described in the "Instruction Manual Model 622SC Fiber Optically Coupled TV System," 1991, Gatan Inc., 6678 Owens, Dr, Pleasanton, Calif. 94588. To pick up an electron microscope image, the imaging instrument is placed on a flange provided at a bottom of a camera chamber 28 of the electron microscope. The imaging instrument comprises an electron-photon converting scintillator 41, optical fiber plates 42, an image intensifier 43, a prior photoconduction-type imaging device 44, an imaging device control system 45, and a monitor 34. One optical fiber plate 42 is placed between the scintillator 41 and image intensifier 43 and the other optical fiber plate 42 between the image intensifier 43 and the photoconduction-type imaging device 44, the both being faced with each other to couple. The prior photoconduction-type imaging device 44 was a imaging tube (representative trade name: Newbicon) having $Zn_{1-x}Cd_xTe$ used for a photoconduction face thereof or a imaging tube (representative trade name: SIT tube) having Si used for a photoconduction face thereof. The quantum effect of both imaging tubes 44 become maximum at a light wavelength of 500 to 750 nm. To make a highly sensitive imaging, the scintillator 41 used for converting an electron image to optical image was the one disclosed in, for example, "Electron Microscopy," Japanese Society of Electron Microscopy, Vol. 27, No. 2, p. 170 (1992). The scintillator 1 has a YAG $(Y_{3-x}Ge_xAl_5O_{12})$ of 550 nm peak luminescence wavelength doped with cerium or GOS $(Gd_2O_2S)$ of 510 nm peak luminescence wavelength doped with praseodymium, cerium, or fluorine.

In FIG. 19, electrons transmitted through specimen (not shown) pass through electron lenses 26, and form an electron microscope image on a fluorescent plate 27, whenever a fluorescent plate 27 closes an opening separating a column 29 and a camera chamber. In operation of the imaging apparatus, at first a fluorescent plate 27 is drawn up from the opening so as to project an electron microscope image onto the scintillator 41.

The scintillator 41 converts electrons to photons. The converted photons are in proportion to intensity of the electron microscope image, or number of the electrons per area. The photons pass the optical fiber plate 42 before coming to the image intensifier 43. The image intensifier 43 converts photons to electrons to magnify-more than 100 times before converting the electrons to photons again. The magnified photons pass the optical fiber plate 42 to the photoconductive-film of the photon reception surface of the photoconduction-type imaging device 44 to emit electron-hole pairs. The generated current is detected by an electron beam emitted from an electron gun of the photoconduction-type imaging device 44 to obtain an output signal. The electron beam is scanned at a TV rate of 1/30 sec per screen. As a result, the electron microscope image on the photoconductive film can be picked up in the same way as an ordinary TV camera.

SUMMARY OF THE INVENTION

With the conventional techniques mentioned above, it is necessary to prepare a large number of thinned pieces having a thickness of the order of several nm by cutting a specimen in various directions. In this case, if a target structure in the specimen has an infinitesimal size of the order of nanometers, it is impossible to cut the structure into a plurality of pieces and, thus, impossible to carry out 3-dimensional observation. Even if the target structure is large enough to allow the thinned pieces to be prepared, only part of the target structure is contained in such a piece so that a lot of information is found missing when constructing a 3-dimensional structure based on the electron microscope images of the pieces. In addition, since the observer has to infer a 3-dimensional structure while taking the relation between observation directions and their electron microscope images of thinned pieces, the technique results in very inadequate precision. The accuracy of the observation directions is effected by errors in the angle setting when specimen pieces are cut out and inclinations of the specimen pieces set on the specimen holder of the electron microscope. It is difficult to make the observation conditions by electron microscopes completely uniform for all the specimen pieces. The resulting errors thus give rise to variations in image contrast. An inference image formed by diffracted electrons, or a lattice image, varies depending upon, among other things, the thickness of the specimen and electron diffraction conditions. In addition, even though information on the atomic arrangement can be obtained from a lattice image, it is difficult to identify the atomic species of impurities and point defects.

In addition, it is disclosed in Japanese Patent Laid-open No. 61-78041 that the electron incidence direction to the specimen surface is fixed and all reflected characteristic X-rays generated in the specimen can be obtained by changing the direction of detection. Information on the structure of a 3-dimensional atomic arrangement close to the surface is thereby obtained. Nevertheless, the obtained information is limited to one to two atomic layers on the surface due to the use of all the reflected characteristic X-rays. In addition, since the characteristic X-rays are generated from a region of the micron order, it is impossible to obtain high resolution at an atomic level. It is thus extremely difficult to obtain a 3-dimensional atomic arrangement in the bulk with a high resolution at an atomic level.

On the other hand, the prior electron detection instrument described above has the fixed shape of the detector. For the annular detector shown in FIG. 18, for example, an angle range of electron detection of $\theta_1$ to $\theta_2$ is determined in terms of a distance (camera length) between the specimen 24 and the scintillator 31. If an enlarging electron lens is placed between the specimen and the detector, the camera length can be varied. However, the angle range of electron detection changes in proportion to the camera length only. It is therefore impossible to set the angle range of electron detection to a desired one. The sole solution is to take the method that a multiple of detectors having different angle ranges of electron detection are prepared and are replaced depending on an observation object. This solution is expensive and takes too much time and labor for replacement and adjustment to use for practical work.

The prior imaging instrument also has the detectors (e.g. scintillators 31) for transmitted electrons and diffraction pattern provided separately from the one for high-angle scattered electrons. This is disadvantageous in that the detectors can serve only for the respective uses. In particular, the detectors for diffracted pattern must have such a multiple of pixels as a CCD (charge-coupled device) camera. The detector cannot be used in common with the prior ones for transmitted electrons and high angle scattered electrons. This means that a user must unavoidably prepare a plurality of exclusive detectors.

The prior imaging instrument for electron microscope (shown in FIG. 19) has the pixels needed to measure the image. The imaging instrument therefore can detect the scattered, diffracted, refracted, or transmitted electrons through a wide range of angle. However, the electron beam emitted from the electron gun of the imaging device 44 (situated bottom of the imaging device, not shown) is usually scanned in a square area on the surface lying along the lower optical fiber plate 42. The imaging instrument is not used as in the annular detector of the electron detection instrument. The detector therefore cannot detect the electron beam in a desired detection angle range. Also, the prior photoconduction-type imaging device 44 used in the imaging section is too low in sensitivity. Therefore, the image intensifier 43 is necessary to magnify the image intensity. The image intensifier 43, however, generate great amount of quantum noises through its magnification process. This results in terribly bad image quality. Such a phenomenon also occurs in the prior above-described electron detection instrument (shown in FIG. 18) since the photons are magnified by the photomultiplier 33. In particular, the electron detection instrument cannot detect the high-angle scattered electron beam at high signal-to-noise ratio since the beam is too weak. Further, if the scintillator 41 is used for the imaging device 44 having a maximum photon reception sensitivity outside the luminescence wavelength of 500 to 700 nm of the scintillator 41, the sensitivity is lowered.

It is a first object of the present invention to obtain a 3-dimensional atomic arrangement and atomic species in the bulk with a high resolution at an atomic level using only a single thin-film specimen and, thus, to allow a 3-dimensional atomic structure to be analyzed accurately in a short period of time.

It is a second object of the present invention to provide an electron detection instrument for electron microscope that can detect an angle distribution of intensity of scattered, diffracted, refracted, or transmitted electrons through a specimen at a high sensitivity and a high signal-to-noise ratio in a desired range of angle.

In order to achieve the first object described above, a system comprising a scanning transmission electron microscope, a specimen goniometer/tilting system, a multi-channel electron detector and a computer was built. The scanning transmission electron microscope includes a unit for radiating an electron beam having a diameter equal to or smaller than the size of one to two atoms. The specimen goniometer/tilting system can be controlled to move a specimen by a distance of the order of nanometers. The multi-channel electron detector allows the range of detection angles of scattered electrons to be arbitrarily set. The computer is used for executing software for controlling the electron microscope and softwares for image processing. The system is thus equipped with facilities for observing a 3-dimensional structure. To speak in more concrete terms, the system is characterized in that some projection images of atomic arrangement are obtained within an angular increment range θ from a predetermined inclination angle. While rotating the specimen over an angle in a range smaller than the angular increment θ, n images of 2-dimensional atomic-arrangement are produced. Note that within the angular range in which the projection image of atomic arrangement is obtained, the so-called channelling phenomenon must occur at least once. In addition, the angular increment θ is equal to $\tan^{-1}(d/t)$, where d is the distance from an atom to an adjacent one in the specimen and t is the thickness of the specimen. From the n images of 2-dimensional atomic-arrangement obtained as such, atomic coordinates with rough precision and atomic species are identified. Next, a 2-dimensional atomic-arrangement image is simulated by the informations.

The simulated image is then compared to the 2-dimensional atomic-arrangement images actually measured. Atomic coordinates and atomic species with high accuracy are obtained as both the images match each other. The accurate atomic coordinates and atomic species are used to display a 3-dimensional atomic-arrangement image.

Accordingly, not only is a 3-dimensional atomic arrangement observed, but a structural analysis can also be performed as well using the same system.

A thin-film specimen is observed using the scanning transmission electron microscope using an electron beam with a diameter equal to or smaller than the size of one to two atoms. The observation can result in an atomic-arrangement image. By observing the specimen while varying its inclination by means of the specimen goniometer/tilting system, atomic-arrangement images from various directions can be obtained. By applying image processing to the atomic-arrangement images obtained for various inclination angles, a 3-dimensional atomic arrangement of the specimen can be constructed and atomic species can be identified from an analysis of a relation between the detection-angle ranges of scattered electrons used in the imaging and the degrees of the image contrast.

In order to achieve the second object described above, and especially improve the accuracy of 3-dimensional atomic arrangement observation and atomic identification described as the first object, the electron detection instrument having a signal reception section in which a signal detection area detecting signals caused by electrons from a specimen with high sensitivity and resolution thereby can be set arbitrarily was used in combination with the electron detection instrument controller controlling the electron detection instrument to set the signal detection area in the signal reception section. The electron detection instrument above mentioned, usually comprises a scintillator and an imaging device. In this case, the imaging device which can set a photodetection area (as a signal detection area) arbitrarily on a photon reception section (as a signal reception section) was employed.

The imaging device used is an avalanche-type imaging device having amorphous-selenium photoconductive-film thereof or a CCD (charge-coupled device). A contour of the photodetection area of the avalanche-type imaging device is set by controlling an electron beam deflecting system to control a contour of scanning the electron beam emitted from an electron gun for signal detection that is equipped in the imaging device. A contour of photodetection area of the CCD is set by selecting activated one of a multiple of pixels arrayed. Each of the contours of photodetection areas of the imaging devices is controlled by a computer to change depending on an angle distribution of intensities of the electrons to be detected.

The scintillator for the avalanche-type imaging device consists of metal oxo silicate doped with cerium with 350 to 450 nm peak luminescence wavelength. A transparent substrate of the imaging device is preferable to be structured to have an optical fiber plate and a flatting layer laminated together.

The flatting layer is formed as follows. An optical fiber plate is painted with liquid or powder glass. A Si single crystal wafer and an optical fiber plate are pressed together, with the wafer fitted with the glass. In pressing, they are heat-treated. After that, the Si single crystal wafer processed in a back-etching way or the flatting layer is formed by thin glass plate stuck with the optical fiber plate by a bond.

Therefore, the electron detection instrument of the present invention can set the photodetection area of the imaging device as needed so that a detection angle range of the electron beam emitted from the specimen can be set as desired. Therefore, intensities of the scattered, diffracted, refracted, or transmitted electrons through the specimen can be detected in the desired angle range depending on the angle distribution of the electrons. The emission angle distribution of the intensities of the scattered electrons depends on an atomic number of an atom of the specimen.

The angle range of detection thus should be set at an angle position at which the scattered electron intensity from the atom is maximum. This makes it possible to enhance the image contrast of the definite atom on the electron microscope image. In particular, if the intensities are detected at a high angle, atomic species determination can be made by quantitatively analyzing the contrasts. The intensity distribution of the diffracted electrons contains information of array of the atoms. This makes it possible to analyze the orientations of the crystal faces, arrays of impure atoms, and shapes and distribution of crystal defects from the position of diffraction spots and the broad pattern.

The detection angle range of the electrons can be set as desired as described above. The detection angle range can be divided into, for example, a central and peripheral areas, from which signals are detected. The central and peripheral areas make it possible to detect the respective transmitted electrons and high-angle scattered electrons simultaneously. As the imaging device has the pixels arrayed in two dimensions, it is possible to measure not only the intensities of the electrons, but also distributions, for example, diffraction pattern and images. Consequently, only one unit of the electron detection instrument of the present invention can measure the high-angle scattered electrons for 3-dimensional atomic arrangement observation and atomic identification, transmitted electrons for conventional electron microscope image, and diffracted electrons for electron diffraction pattern.

The electron detection instruments of the present invention can also measure a weak electron beam at a high accuracy and high signal-to-noise ratio with use of the avalanche-type imaging device having an amorphous-selenium photoconductive-film thereof as the imaging device and with use of the metal oxo silicate doped with cerium as the electron-photon converting scintillator without the photomultiplier and image intensifier to intensify the beam. The reason is explained below.

FIG. 7 depicts a table illustrating characteristic comparisons of the photomultiplier, the prior photomultiplier type imaging device, and the avalanche-type imaging device having an amorphous-selenium photoconductive-film thereof. It is defined here that primary quantum efficiency is number of photoelectrons produced when one photon comes in the photoconductive-film. It is also defined that multiplication factor is a ratio of current output of the imaging device to current of the photoelectrons. The primary quantum efficiency is determined by material of the photoconductive-film. The photoconductive-film of the photomultiplier is formed of $Na_2KSb$-Cs, that of the prior photoconduction-type imaging device of $Sb_2S_3$, ZnCdTe, or the like, and that of the avalanche-type imaging device of amorphous Se. We can see from the figure that the amorphous Se has the highest efficiency in converting the photon to photoelectron. The multiplication factor of photomultiplier is ordinarily around $10^5$ times since the electrons produced in the photoconductive-film are multiplied by a multiple of diode stages. The prior photoconduction-type imaging device cannot multiply the electrons since its photoconductive-film is formed of $Sb_2S_3$, ZnCdTe, or the like. The avalanche-type imaging device does avalanche multiplication of the electrons in the photoconductive-film by applying a high electric field of around $10^6$ V/cm to the photoconductive-film. The multiplication factor achieved is 1,000 times at maximum, depending on the electric field applied to the photoconductive-film (FIG. 8). The sensitivity is a product of the primary quantum efficiency by the multiplication factor. The photomultiplier therefore has the highest sensitivity, but is low in the signal-to-noise ratio that determines the image quality. The reason is that the primary quantum efficiency is low and high noises are produced when little photoelectrons are forcibly photomultiplied by the diodes. The prior photoconduction-type imaging device has not a high primary quantum efficiency, but is high in the signal-to-noise ratio since the multiplication factor is 1. As the sensitivity is low, however, the image intensifier is inevitable together to detect weak electron beam that forms the electron microscope image. If the image intensifier magnifies the electrons 100 times, for example, extensive quantum noises appear, resulting in extreme deterioration of the signal-to-noise ratio. On the other hand, the avalanche-type imaging device having an amorphous-selenium photoconductive-film thereof provides high sensitivity and signal-to-noise ratio enough to measure the electron microscope image. The reason for the high signal-to-noise ratio is that the primary quantum efficiency is high and excessive noises are quite low as well. The excessive noises depend on a ratio of the electrons produced in the photoconductive-film to an ionization constant of the holes. As the ratio is high, the excessive noises are high. The amorphous selenium is featured in that the ratio is lower than the other materials with a high electric field applied.

FIG. 9 depicts a graph illustrating the relative sensitivity of the avalanche-type imaging device having an amorphous-selenium photoconductive-film thereof. We can see from the figure that the relative sensitivity is highest at light wavelength of 400 nm. The light wavelength for maximum emission therefore is 420 to 430 nm with use of the metal oxo silicate (chemical formula: $RE_2SiO_5$) doped with cerium as the electron-photon converting scintillator, particularly with RE being Gd, Y, or Lu. By using the scintillators, the primary quantum efficiency of the image device becomes higher than 98%. The sensitivity of the imaging device of the electron noise can be obtained to the maximum limit.

The optical lenses in the optical system of electron detection instrument can be eliminated by the way that the transparent substrate of the imaging device is structured to have the optical fiber plate and the flatting layer laminated together. This can reduce so high a light intensity loss due to the optical lenses that the detection sensitivity of the electron beam can be increased as much as about five times. The flatting layer also provides the following advantage. The optical fiber plate has minute irregularities of around 0.2 μm remained on the surface only after the plate is optically polished. The avalanche-type imaging device having the sensitivity leaped greatly high that is a high-sensitivity image tube, has the electric field concentrated at the irregularity because of high operation electric field. The concentration destructs the dark current preventive function locally. As a result, it is a problem that the local dark current is increased, which causes white scratches on the image. The above-mentioned flatting layer can reduce the concentration of the electric field to the irregularities on the surface to a great extent since the irregularities is less than 10 nm, thus thereby successfully solving the above-mentioned problem

BRIEF DESCRIPTION OF THE DRAWINGS

FIG. 1(a) shows states of transmission and scattering electron beams and an electron-microscope image when electron beam is parallel to the direction of atomic columns. FIG. 1 (b) shows states of transmission and scattering electron beams and an electron-microscope image when electron beam has an incident angle θ to the direction of the atomic columns;

DETAILED DESCRIPTION OF THE PREFERRED EMBODIMENTS

Referring to the diagrams described briefly above, embodiments according to the present invention are explained as follows.

[EMBODIMENT 1]

Figure 5:
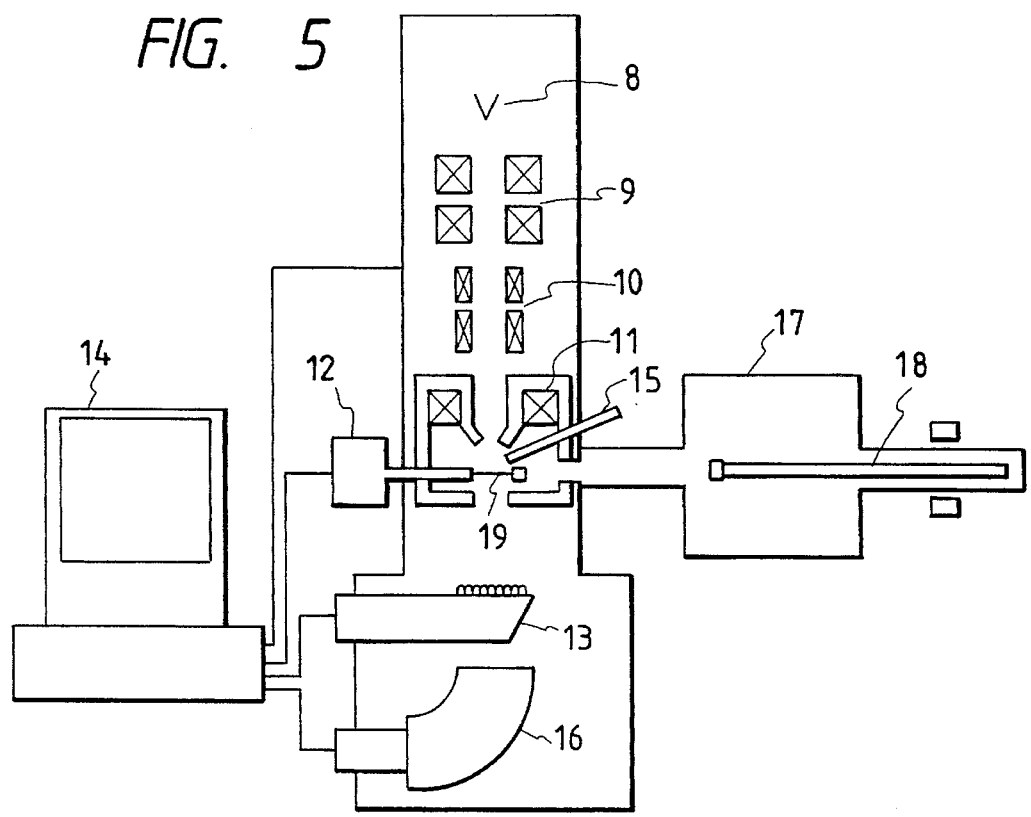
FIG. 5 is a diagram showing an overall structure of the embodiment 1 according to the present invention.

FIG. 5 is a diagram showing a basic configuration of an electron-microscope apparatus used in the embodiments according to the present invention. As shown in the figure, the apparatus comprises a field emission electron gun 8, condenser lenses 9, electron deflector coils 10, object lenses 11, a specimen goniometer/tilting system 12, an electron detector 13, a computer 14 for executing control and image-processing software, an X-ray detector 15, an energy analyzer 16, a specimen preparation room 17 and a specimen transfer system 18. In order to generate an electron beam with a diameter equal to or smaller than the size of one to two atoms, an acceleration voltage of at least 200 kV is applied to the field emission electron gun 8 and electrostatic lenses and magnetic lenses (as 9–11) for illumination with small aberration are employed. A specimen 19 is scanned by the beam deflecting/scanning coil 7 by applying an electron beam to the specimen 19. The electron detector 13 has a multi-channel typed matrix of a plurality of photosensitive devices. The intensities of electrons scattered and transmitted by the specimen 19 can be measured by identifying relations between the addresses of the photosensitive devices in the matrix and the scattering angles and directions of the electrons. Even though CCD photosensitive devices are typically employed in the electron detector 13, photosensitive devices of other types with high sensitivity can also be used as well. The specimen goniometer/tilting system 12 comprises a step motor and a goniometer which are controlled by the computer 14. This allows the inclination of the specimen 19 to be adjusted in the milliradian order. So, the positional aberration is compensated in the nanometer order. The computer 14 executes the control and image-processing software, allowing intensities and distribution of electrons measured by the electron detector 13 to be input and stored into memory in synchronization with the scanning operation of the incident electron beam. In addition, the computer 14 is also capable of carrying out a variety of image processings.

Figure 1:
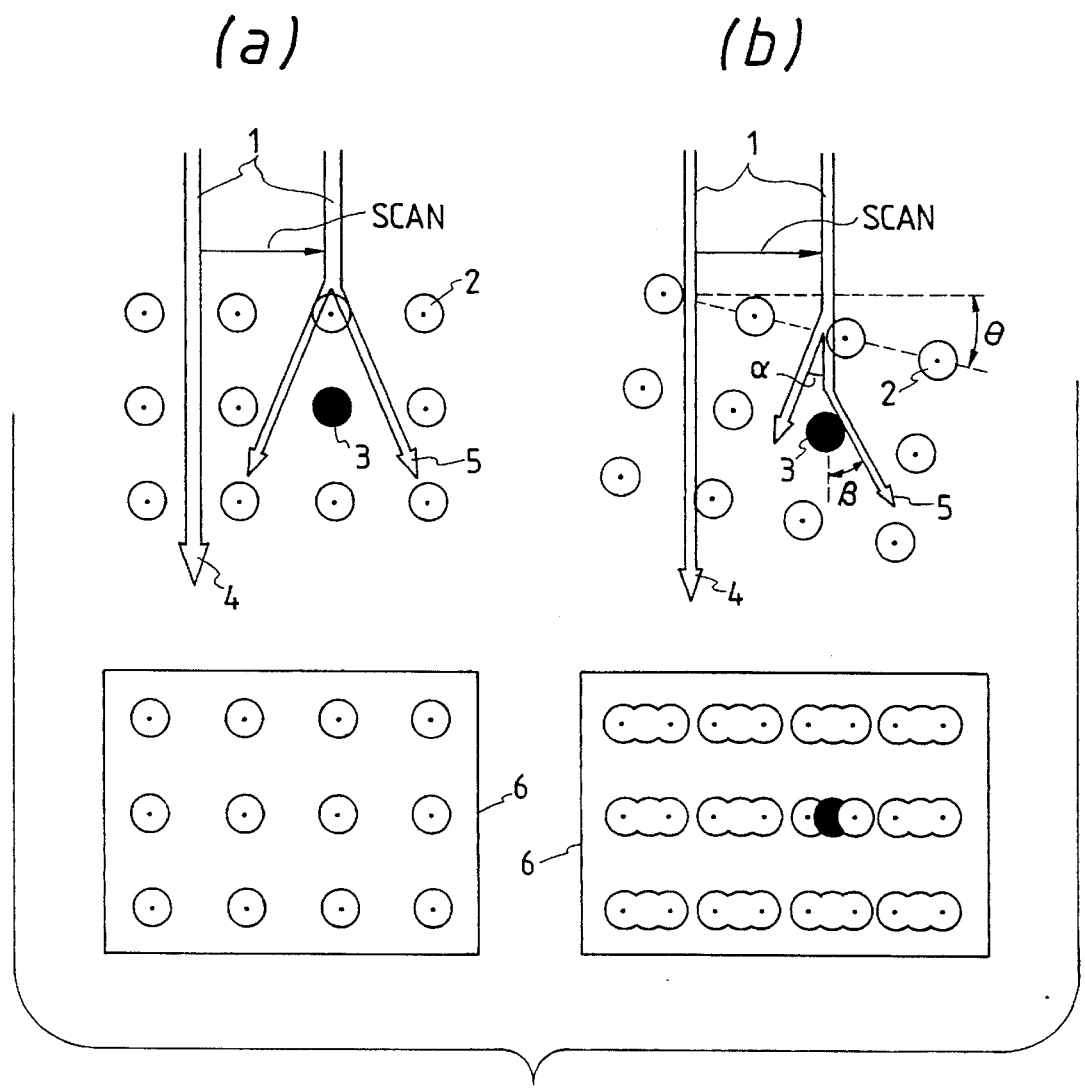
FIG. 1 is an explanatory view showing the principle of image formation using an electron beam with a diameter equal to or smaller than the size of one to two electrons.
Figure 2:
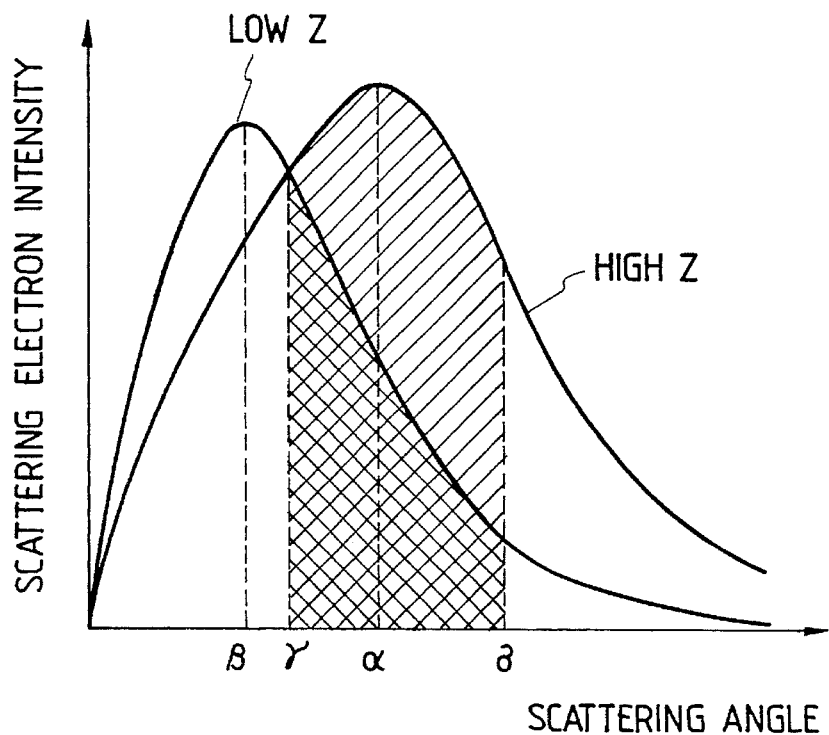
FIG. 2 is an explanatory view showing relations between the scattering electron intensity and the scattering angle for atoms with low and high atomic numbers.
Figure 3:
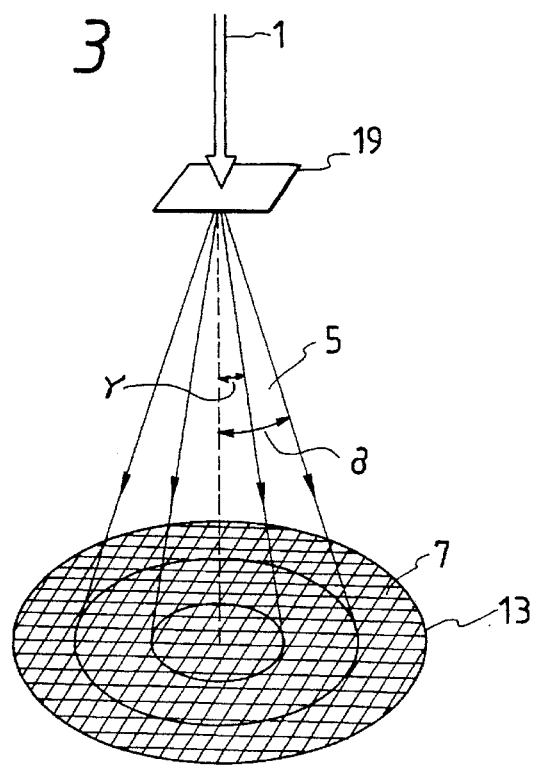
FIG. 3 is an explanatory view for measurement of scattering electrons by a multi-channel electron detector in a scattering angle between γ and δ.
Figure 6:
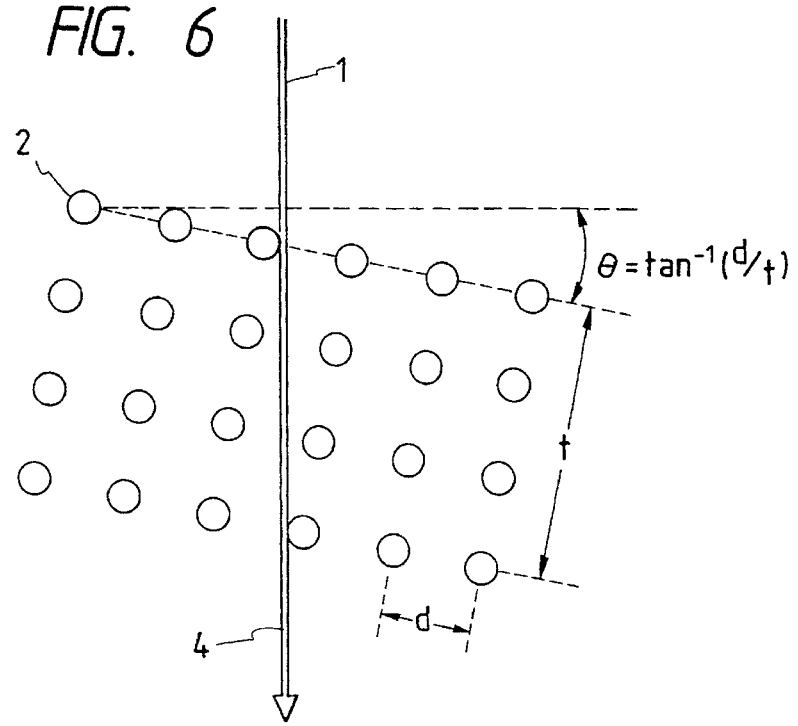
FIG. 6 is an explanatory diagram showing a relation between the angular increment (θ) of the specimen, the distance from an atom to an adjacent one (d) and the thickness of the specimen (t)
Figures 7, 9:
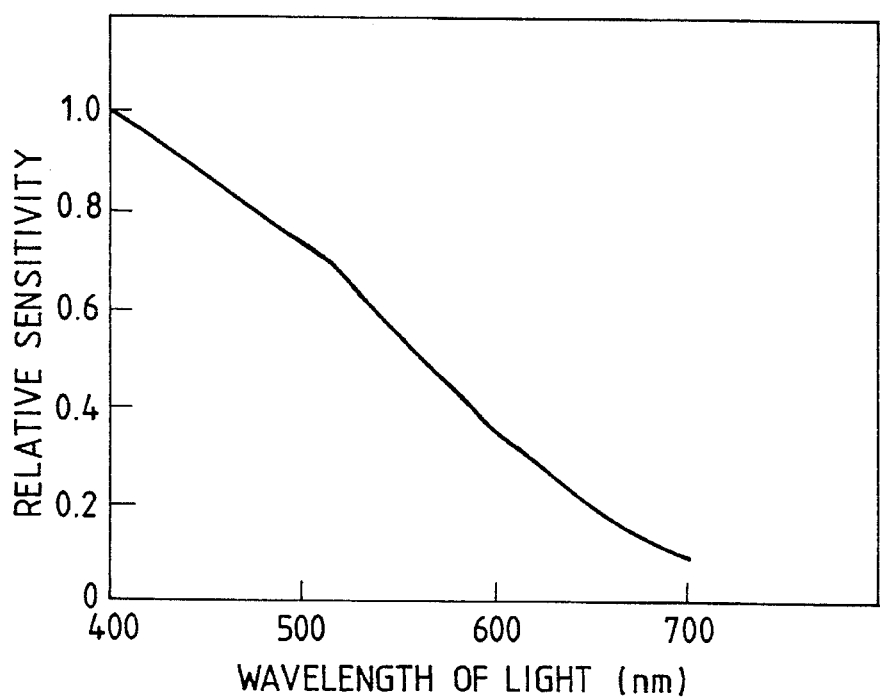
FIG. 7 is a table illustrating characteristic comparisons of a photomultiplier, a prior photoconduction-type imaging device, and an avalanche type imaging device having amorphous-selenium photoconductive-film thereof.
FIG. 9 is a graph illustrating a relative sensitivity of the avalanche-type imaging device having amorphous-selenium photoconductive-film thereof.
Figure 8:
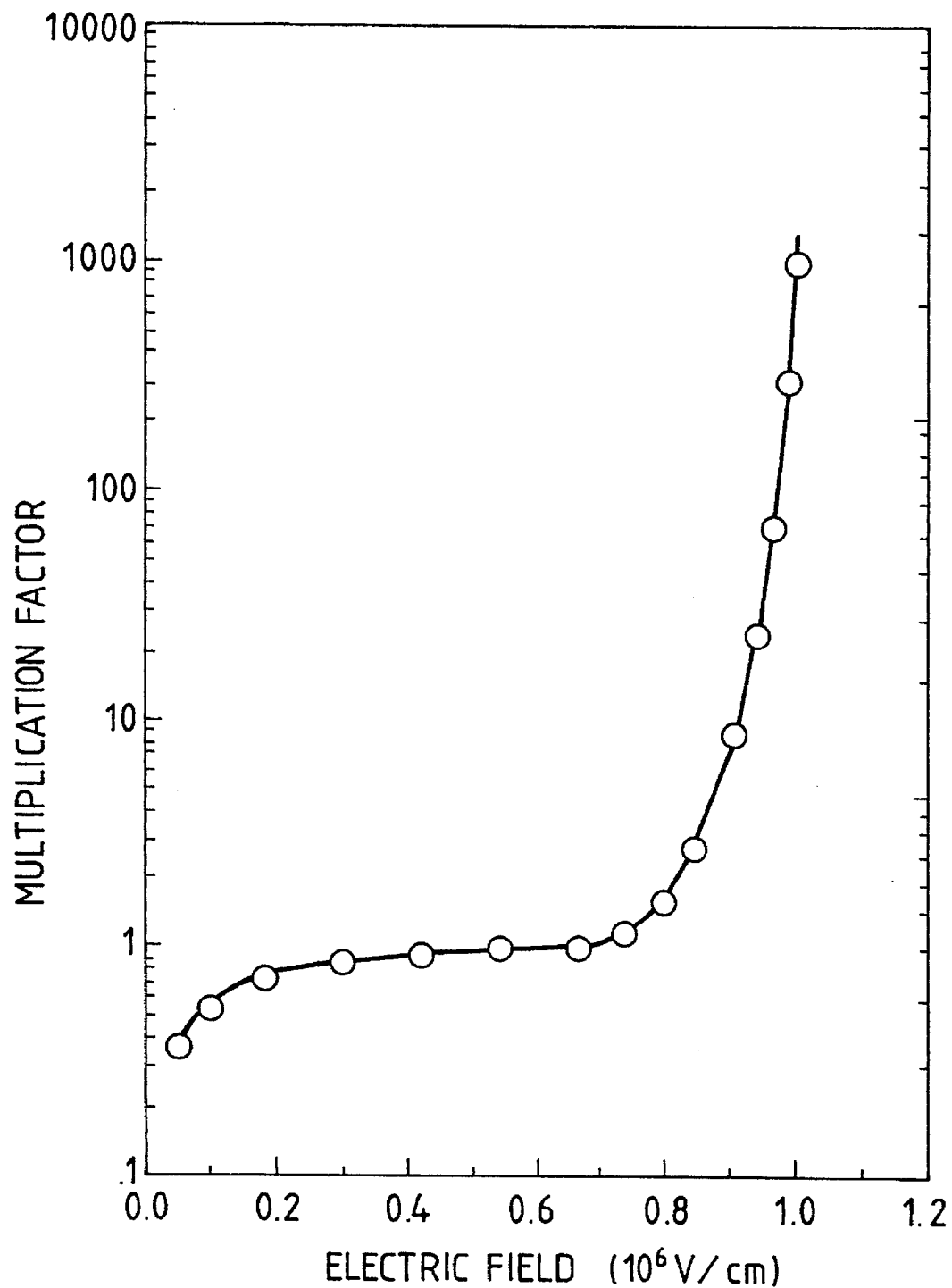
FIG. 8 is a graph illustrating a multiplication factor to an electric field of the avalanche-type imaging device.

Next, a step of observing a 3-dimensional atomic arrangement according to the present invention is described. FIG. 1 shows interaction between an atom 2 constituting the thin-film specimen 19 and incident an electron beam 1 having a diameter equal to or smaller than the size of one to two atoms. FIG. 1 (a) shows a case in which the incident electron beam 1 is parallel to the direction of the atomic columns of the thin-film specimen 19. In this case, an electron incident beam 1 between two adjacent atomic columns is transmitted through by a channelling phenomenon without being scattered by the atoms 2. Note that the channelling phenomenon is a phenomenon in which an electron beam 1 is passed through. An incident electron beam 1 hitting an atomic column is scattered by the first atom 2 on the atomic column. By measuring the intensity of a transmitted or scattered electron 4 or 5 in synchronization with the scanning operation of the incident electron beam 1 by means of the electron detector 13, a projection image of atomic arrangement 6 can thus be observed. Next, the thin-film specimen 19 is inclined to form an angle θ with the incident electron beams 1. As shown in FIG. 6, the angle θ is set to a value smaller than $\tan^{-1}(d/t)$, where d is the distance from an atom to an adjacent one on the thin-film specimen 19 and t is the thickness of the thin-film specimen 19. Though the gap between two adjacent atomic columns as seen from the incident direction of the electron beams 1 becomes smaller, a channelling electron exists. As shown in FIG. 1(b), the projection image of the arrangement 6 corresponds to a projection image viewed from an inclined direction forming the angle θ with the atomic columns. In this case, the view of an impure atom 3 is different from that of FIG. 1(a). That is to say, the impure atom 3 in FIG. 1(a) is not visible because it is shadowed by an atom 2 located right above it. In the case shown in FIG. 1(b), however, the different atom 3 is visible. Accordingly, the incident electron beam 1 is scattered also by the impure atom 3. In general, relations between the scattering angle and the intensity of a scattered electron are shown in FIG. 2. As shown in the figure, the scattered electron intensity is distributed among the scattering angles with a peak located at certain scattering-angle values. The distribution curves are flatter for high scattering-angle values. The distribution curves are also different from each other depending upon the atomic number (Z). The larger the value of the atomic number (Z), the more the distribution curve is shifted to the side of large scattering-angle values. Accordingly, a scattering angle β for the peak intensity of electrons 5 scattered by the impure atom 3 is different from a scattering angle α for the peak intensity of electrons scattered by a surrounding atom 2. In this case, the atom 2 has a greater atomic number than the impure atom 3. Taking the distribution shown in FIG. 2 into consideration, the detection angle range of the scattered electrons 5 used in the imaging by the electron detector 13 is set between angles γ and δ shown in the figure. FIG. 3 shows a state of operation of the electron detector 13 for the detection angle range between γ and δ. As shown in the figure, the electron detector 13 has a multi-channel matrix configuration which comprises a plurality of photosensitive devices 7.

When the incident electron beam 1 hits the specimen 19, electrons 5 are scattered at a variety of scattering angles, arriving at the electron detector 13. Only electrons with scattering angles between γ and δ are used for creating a projection image of atomic arrangement 6. That is to say, only the intensities of scattered electrons 5, which are detected by photosensitive devices 7 located between two concentric circles corresponding to the scattering angles γ and δ, are measured in synchronization with the scanning operation of the incident electron beam 1. The range of detection angles is set by specifying the addresses of the photosensitive devices 7 with the computer 14. With such measurement, the difference in contrast between atoms on the projection image can be recognized. In this case, the atom 2 is bright whereas the different atom 3 is dark. By embracing the same principle, the difference can still be recognized even if a vacancy exists at the position of the impure atom 3. Information on distribution of scattered electron intensities for various atoms are stored in the computer 14. Accordingly, the detection angle ranges for the various atoms can be set in the electron detector 13. The various atoms can thus be distinguished from each other based on differences in image contrast between them. In addition, since the specimen goniometer/tilting system 12 allows the inclination angle of the specimen 19 to be controlled in the milliradian order, an inclination angle can be set at the condition of the channelling-phenomenon. Moreover, the position of the specimen 19 can be controlled using the computer 14 so that the target of observation on the specimen 19 is always located at the center of the observation area. The computer-based control is carried out by finding the amount of aberration in the position of the specimen 19, that results with the specimen 19 inclined, using the image processing. By continuously observing images while varying the inclination angle and storing image data in the computer 14, the projection images of atomic arrangement 6 observed from a variety of directions can be obtained.

Figure 4:
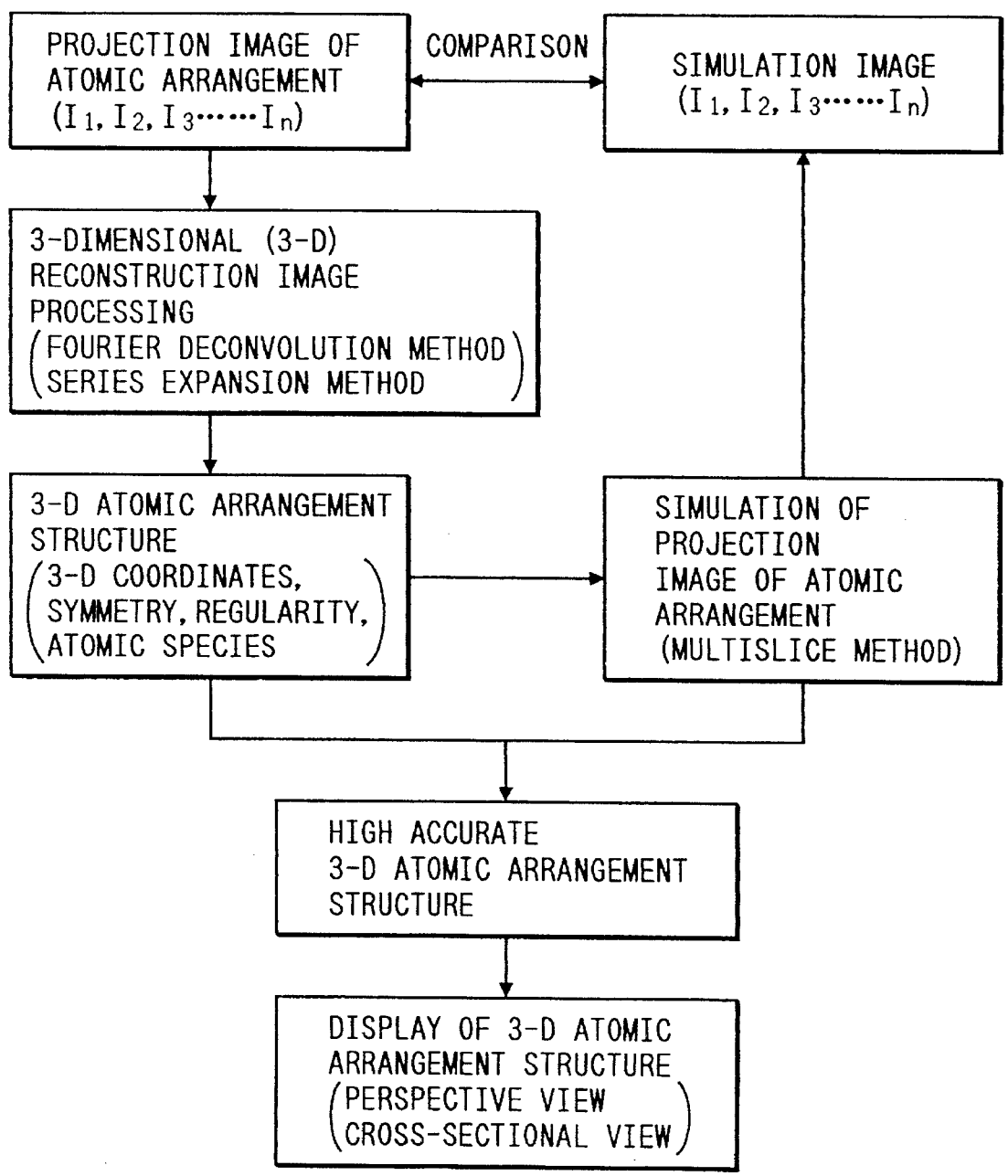
FIG. 4 is an explanatory view showing a process of constructing a 3-dimensional atomic structure by image processing of 2-dimensional atomic images observed at a variety of inclination angles θn of a specimen.

The image processing constructs a 3-dimensional structure of the atomic arrangement based on projection images of atomic arrangement 6 ($I_1$, $I_2$ to $I_n$) obtained at inclination angles ($\theta_1$, $\theta_2$ to $\theta_n$) respectively with a procedure shown in FIG. 4. The 3-dimensional structure of the atomic arrangement is displayed on a CRT of the computer 14. On the procedure, at first, 3-dimensional image processing is performed on the projection images of atomic arrangement 6 ($I_1$, $I_2$ to $I_n$) to identify 3-dimensional coordinates, the symmetry, and the regularity of the atoms. The atomic arrangement identified above are then combined with measurement data of atomic species to determine a 3-dimensional structure of the atomic arrangement of the specimen 19. The technique adopted for constructing the 3-dimensional structure is the same as that described on Page 15 of No. 6, Vol. 17, 1978 of Measurement and Control, a technical journal. The image processing software for constructing the 3-dimensional structure, which is capable of creating a 3-dimensional configuration based upon information obtained even from a range of possible inclination angles 0 to about 20 degrees of a specimen. For example, the softwares are Fourier deconvolution method and the series expansion method. The image processing software is executed by the computer 14 which selects one of the techniques in accordance with the amount of information to be processed. Based on data of the 3-dimensional structure of the atomic arrangement, a projection image of the atomic arrangement 6 is then simulated. Software used in the simulation applies a typical method such as the multi-slice technique. The simulated image is then compared to the observed image in order to confirm whether or not a projection image of the atomic arrangement 6 can be reproduced from the constructed 3-dimensional structure of the atomic arrangement. If the reproduction is impossible, the data of the 3-dimensional structure of the atomic arrangement is corrected to give another simulated projection image of the atomic arrangement 6. This operation is repeated until the simulated image matches the observed one. In this way, the accuracy of the 3-dimensional structure of the atomic arrangement can be enhanced. The 3-dimensional structure of the atomic arrangement determined as such is finally displayed on the CRT of the computer 14 as a squint image or a cross-sectional view seen from any desired direction.

The composition and bonding state of elements constituting the specimen 19 can be analyzed by measurement of a characteristic X-ray by the X-ray detector 15 and measurement of loss energy of transmitted electrons by the energy analyzer 16. A scanning tunnelling microscope is installed at the specimen preparation room 17 in which the thinning process of the specimen 19 is carried out by utilizing a field-evaporation effect that occurs when a field is applied to an area between a tip and the specimen 19. In this way, atoms are stripped off one by one. Accordingly, the thickness of the specimen 19 can be controlled in atomic-layer order without damaging the specimen 19 at all. By carrying out the operation to strip off atoms as such while observing the specimen 19 through the scanning tunnelling microscope, the structure of an infinitesimal portion of interest can be surely converted into a thin film with an accuracy at the atomic level. Since the thin-film specimen 19 is conveyed by the specimen transfer system 18 to a specimen observation room through a vacuum, the specimen 19 is neither contaminated nor oxidized. In the specimen preparation room 17, the specimen 19 can undergo manufacturing and fabrication processes such as the specimen cleaning and alteration using ion radiation and heating and the thin-film formation using evaporation and sputtering. Therefore, atomic structures in a variety of states can be observed. Furthermore, the specimen preparation room 17 can be removed from the electron microscope and connected to the actual thin-film equipment used in the semiconductor process. In such an arrangement, a specimen formed by the thin-film equipment is conveyed to the apparatus provided by the present invention in which the evaluation of its process conditions can be carried out.

As described above, the present invention allows the observation of the 3-dimensional atomic arrangement at a high resolution of higher than 0.2 nm. The present invention also allows the analysis of atomic species. In addition, the present invention allows the composition and the bonding state to be measured as well. Point defects, impure atoms and their clusters which are difficult to examine using the conventional electron microscope can thereby be observed at a single-atomic level. Accordingly, the causes of ULSI devices' defects, thin film's formation conditions and the like can be evaluated at high accuracy. In the case of the conventional electron-microscope techniques, as many specimen samples as numerous observation directions have to be prepared in order to accomplish 3-dimensional observation. With the present invention, however, only a single specimen is required. As a result, the T. A. T. (turn-around time) of the evaluation process is substantially reduced as compared to that of the conventional techniques.

[EMBODIMENT 2]

Figure 10:
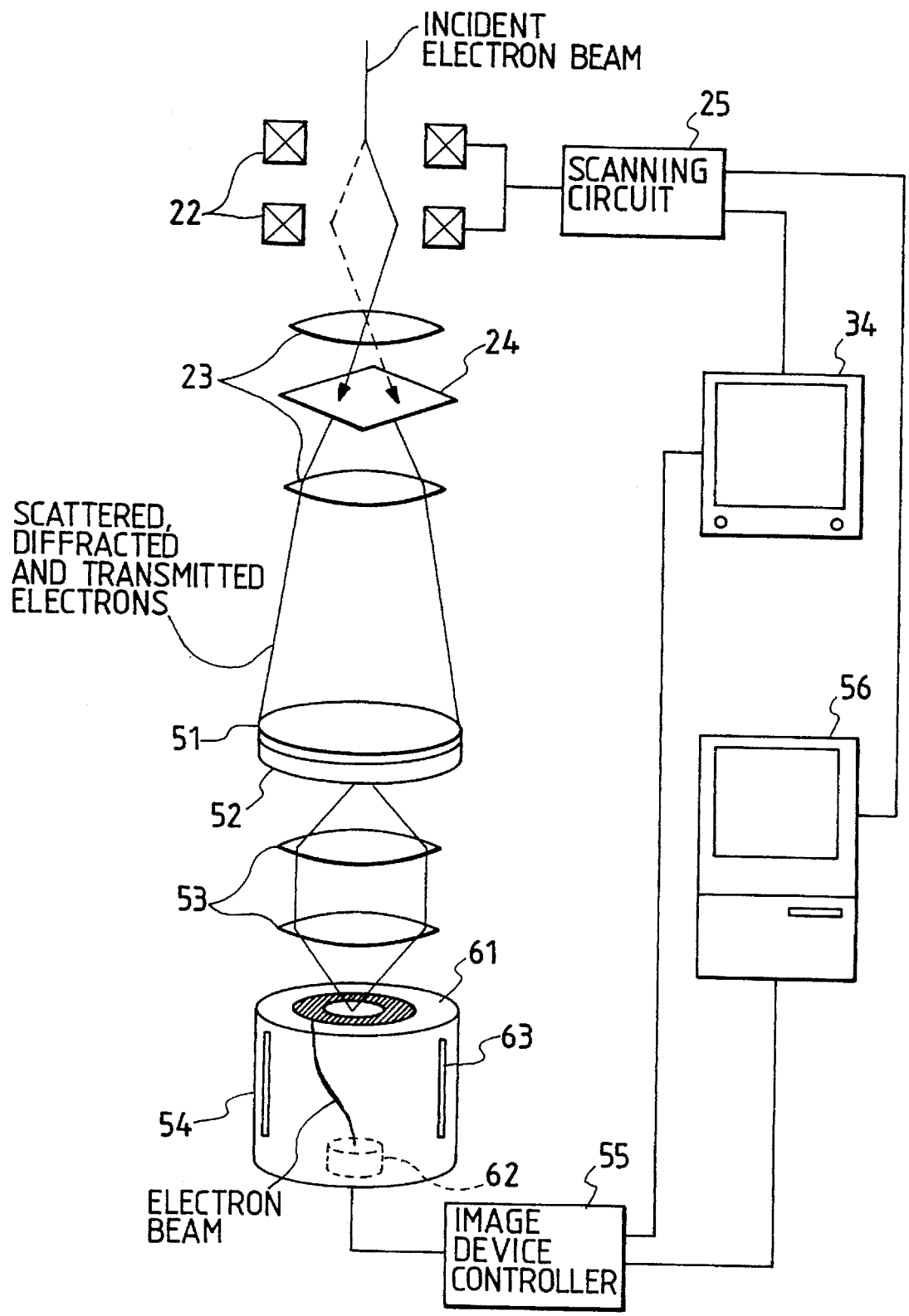
FIG. 10 is an exploded perspective view and a block diagram illustrating an overall configuration of an electron detection instrument for electron microscope used in a first embodiment according to the present invention.

FIG. 10 depicts an exploded perspective view and a block diagram illustrating a basic configuration of an electron detection instrument for electron microscope used in this embodiment according to the present invention. The electron microscope used in this embodiment (overall structure is not shown in FIG. 10) has almost same structure as the embodiment 1 except for the electron detection instrument. The electron detection instrument comprises a scintillator 51, a substrate (e.g. a transparent substrate) 52, optical lenses 53, an avalanche-type imaging device 54 having a photoconductive-film of amorphous selenium, an imaging device control system 55, a computer 56, and a monitor 34. The computer 56 and the monitor 34 are connected with a scanning circuit 25 for energizing deflection coils 22 that scan an incident electron beam of the electron microscope on a specimen 24. The computer 56 and the monitor 34 can have a scanning signal input from the scanning circuit 25. The computer 56 can also synchronize the imaging device 54 through its control system 55 with the scanning circuit 25.

The scintillator 51 is a converter for converting to light intensity distribution an intensity distribution of scattered, diffracted, refracted, or transmitted electrons through the specimen. In this embodiment, the avalanche-type imaging device 54 having the photoconductive-film of amorphous selenium is used. Accordingly, a scintillator 51 material used is a metal oxo silicate doped with cerium that has a luminescence wavelength at which the imaging device has a highest primary quantum efficiency. Conditions for the scintillator 51 include high photon emission, little deterioration, and narrow expansion of incident electron beam accelerated by 100 to 300 keV. The above-mentioned scintillator 51 meets those conditions. The crystal may be either of polycrystal or single crystal. The scintillator 51 should be made several ten μm in thickness so that the incident electron beam should not become wide not to make fuzzy the electron microscope image. The scintillator 51 should have an Al film of several ten nm evaporated on a surface thereof to prevent charge-up.

The optical lenses 53 are used for focusing on a photon reception surface of the avalanche-type imaging device 54 the electron microscope image converted to photon image by the scintillator 51. The lenses used should be short focal distance and low F value relative to an aperture thereof to make little light intensity loss. The above-mentioned optical lenses 53 should be focused on a bottom of an optical fiber plate if the substrate 52 of made of the optical fiber plate or on a bottom of the scintillator 51 if the substrate 52 of made of glass. The latter can make lower the light intensity loss and increase the sensitivity of the electron detection instrument. The lower lens should be focused on the photoconductive-film 61 of the avalanche-type imaging device 54.

In the avalanche-type imaging device 54 the photons produced by the scintillator 51 emit electron-photon pairs in the photoconductive-film 61 of the photon reception surface thereof (upper surface in FIG. 10). The generated current is detected by an electron beam emitted from an electron gun 61 of the avalanche-type imaging device 54 to obtain an output signal. The photoconductive-film 61 makes an avalanche multiplication of the current produced by the incident photons as a higher electric field than $10^6$ V/cm is applied between its upper surface and lower surface (electric applying means is not shown). The avalanche-type imaging device 54 thus can obtain a gain higher than 60 times the ordinary imaging device. The electron beam is scanned on the lower surface of photoconductive-film 61 at a TV rate of $\frac{1}{30}$ sec per screen. The intensity distribution of the photons projected to the photoconductive-film 61 therefore can be picked up in the same way as an ordinary TV camera.

Figure 18:
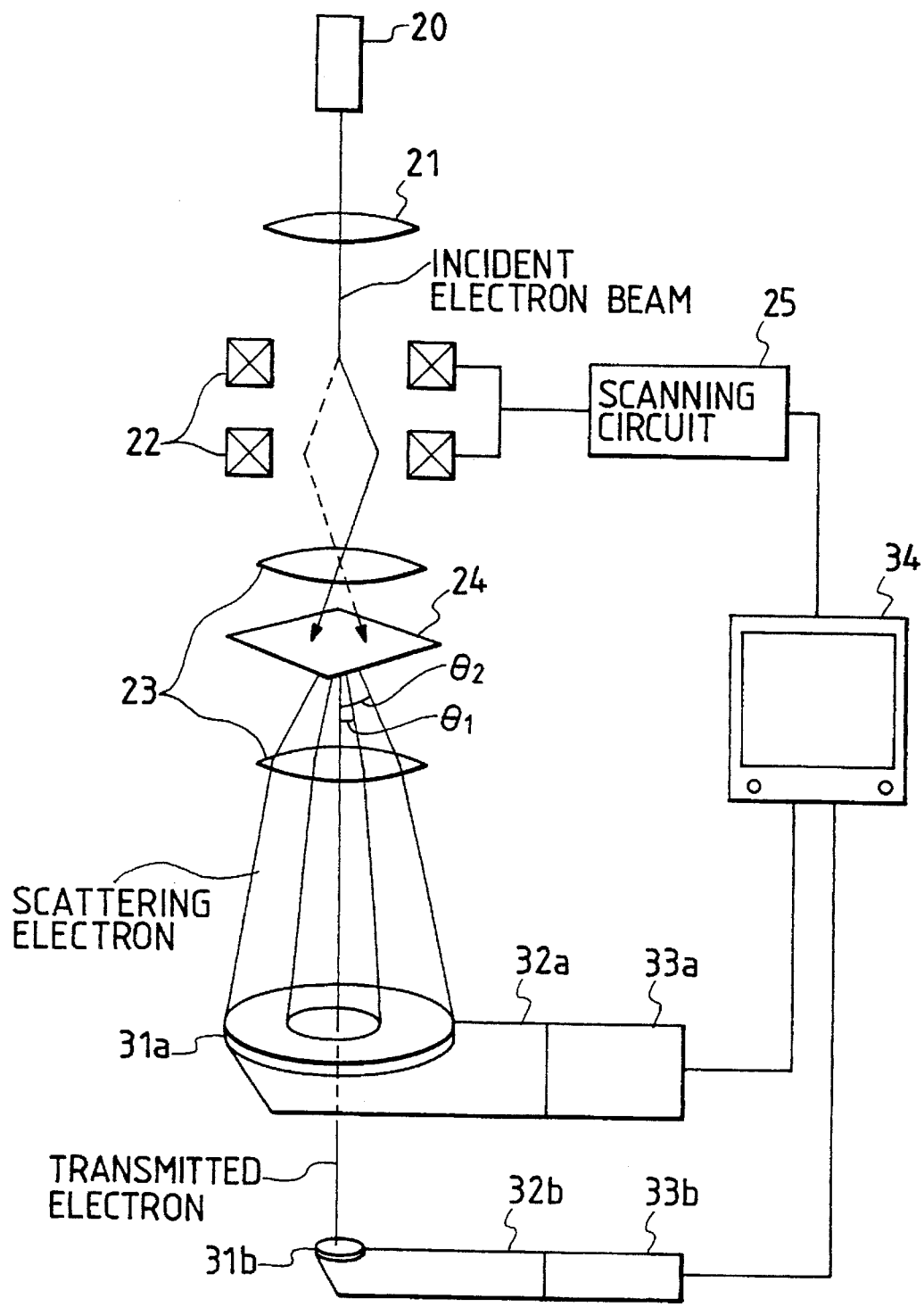
FIG. 18 is an exploded perspective view and a block diagram illustrating an overall configuration of a prior electron detection instrument implemented in an electron microscope.
Figure 19:
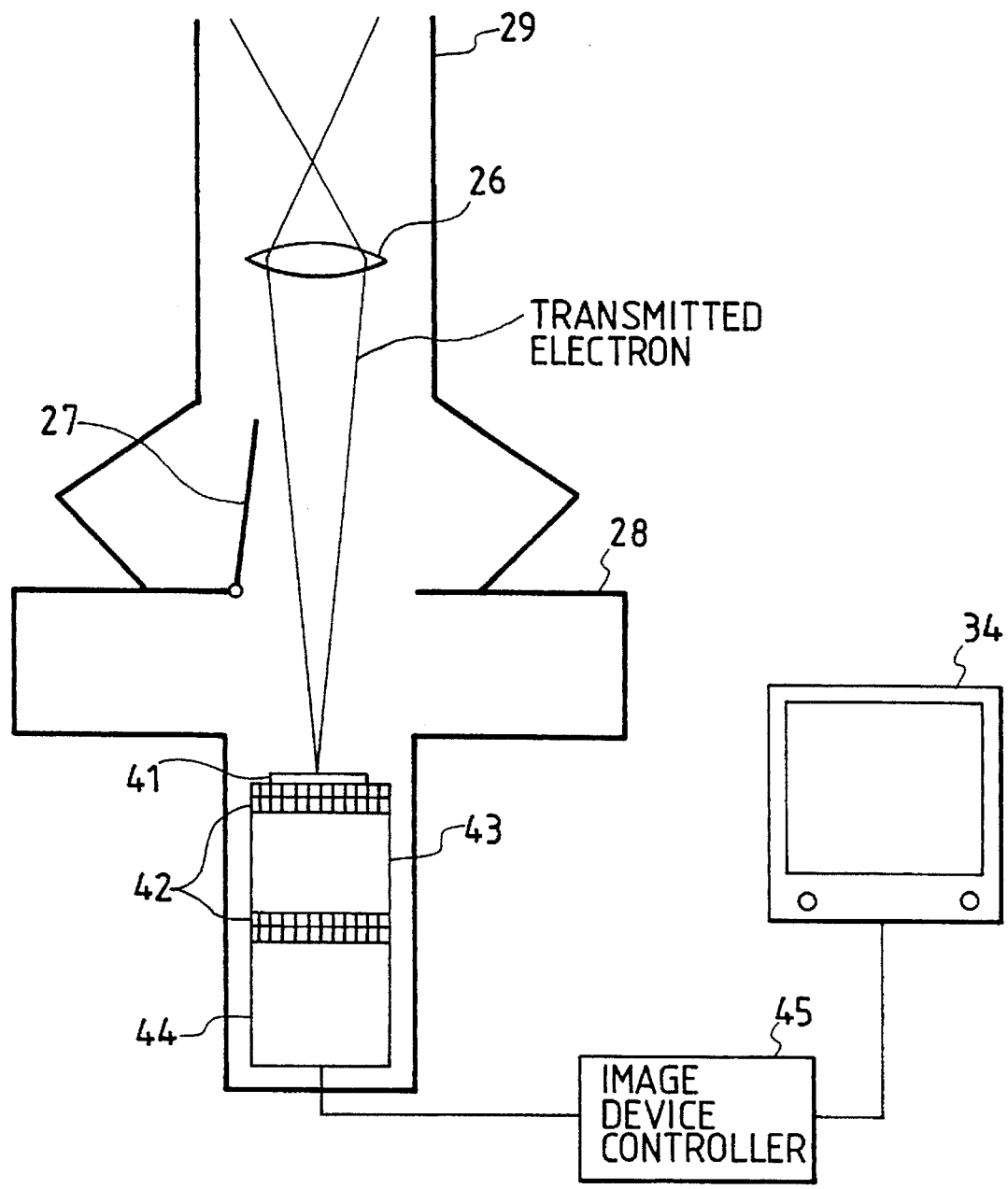
FIG. 19 is an exploded perspective view and a block diagram illustrating an overall configuration of a prior imaging instrument implemented in an electron microscope.

The imaging device control system 55 controls the input and output of the avalanche-type imaging device 54. The imaging device control system 55 controls the deflection electrodes 63 for scanning the electron beam for signal detection to set a contour of detectable area of the whole area of the photoconductive-film 61. If the contour of detectable area is controlled as an annular, the electron detection instrument operates as annular detector for observing a dark-field image only with electrons scattered at the high angle shown in FIG. 18. Similarly, the electron detection instrument also operates as circular detector for observing a bright-field image only with transmitted electrons.

Figure 11:
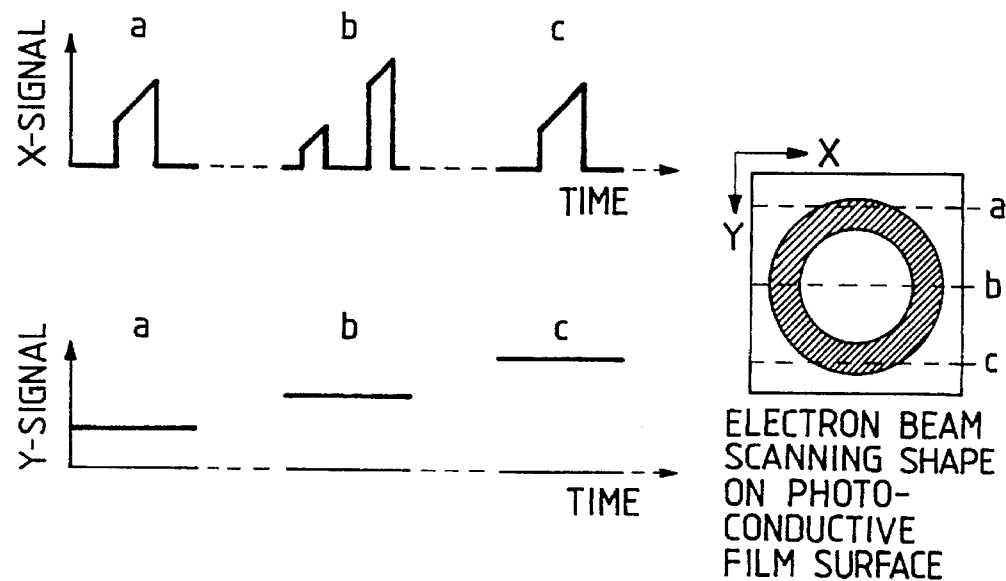
FIG. 11 is waveform graphs illustrating control signals in directions X and Y with an electron beam annularly scanned.
Figure 12:
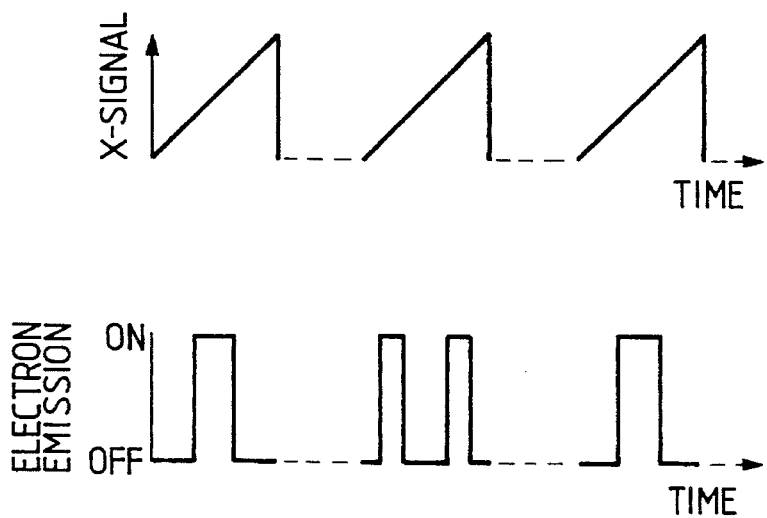
FIG. 12 is waveform graphs illustrating another example of control method for the same scanning pattern as in FIG. 7.

The above-mentioned electron beam for signal detection is controlled as follows. FIG. 11 depicts waveform graphs illustrating control signals in directions X and Y with the electron beam scanned annularly. Symbols a to c indicated above the control signal waveforms correspond to positions a to c of a pattern of the scanned electron beam shown right. FIG. 12 depicts waveform graphs illustrating another example of control method for the same scanning pattern as in FIG. 11. The figure shows only the graphs in the direction X as the control signal waveforms in direction Y are same as in FIG. 11. In the method in FIG. 12, the electron beam emission of the electron gun is controlled at the same time as the scanning control of the electron beam. This can obtain the same scanning pattern as in FIG. 11.

With the avalanche-type imaging device 54, the scanning position of the electron beam for signal detection corresponds to the pixel position. The size of pixel, or resolution, is around 10 μm, depending on diameter of the electron beam for signal detection. Signals output of the imaging device control system 55 can be obtained from the pixels independently. By adding the signals output from the pixels in operation, the intensity of all the detected electron can be measured. If the signals of the pixels are detected in accordance as array of the pixels, they become image information.

The computer 56 controls the imaging device control system 55 and A–D converts and records the electron beam intensity signal and the image signal fed from the imaging device control system 55. The recording is made in correspondence to the scanning position of the incident electron beam on the specimen on the basis of the signal from the scanning circuit 25. The monitor 34 can either display the image signal from the imaging device control system 55 as image directly, for example, an electron diffraction pattern, or display the STEM (scanning transmission electron microscope) image in a way that the electron beam intensity signal is synchronously brightness-modulated with the scanning signal from the scanning circuit 25.

Figure 13:
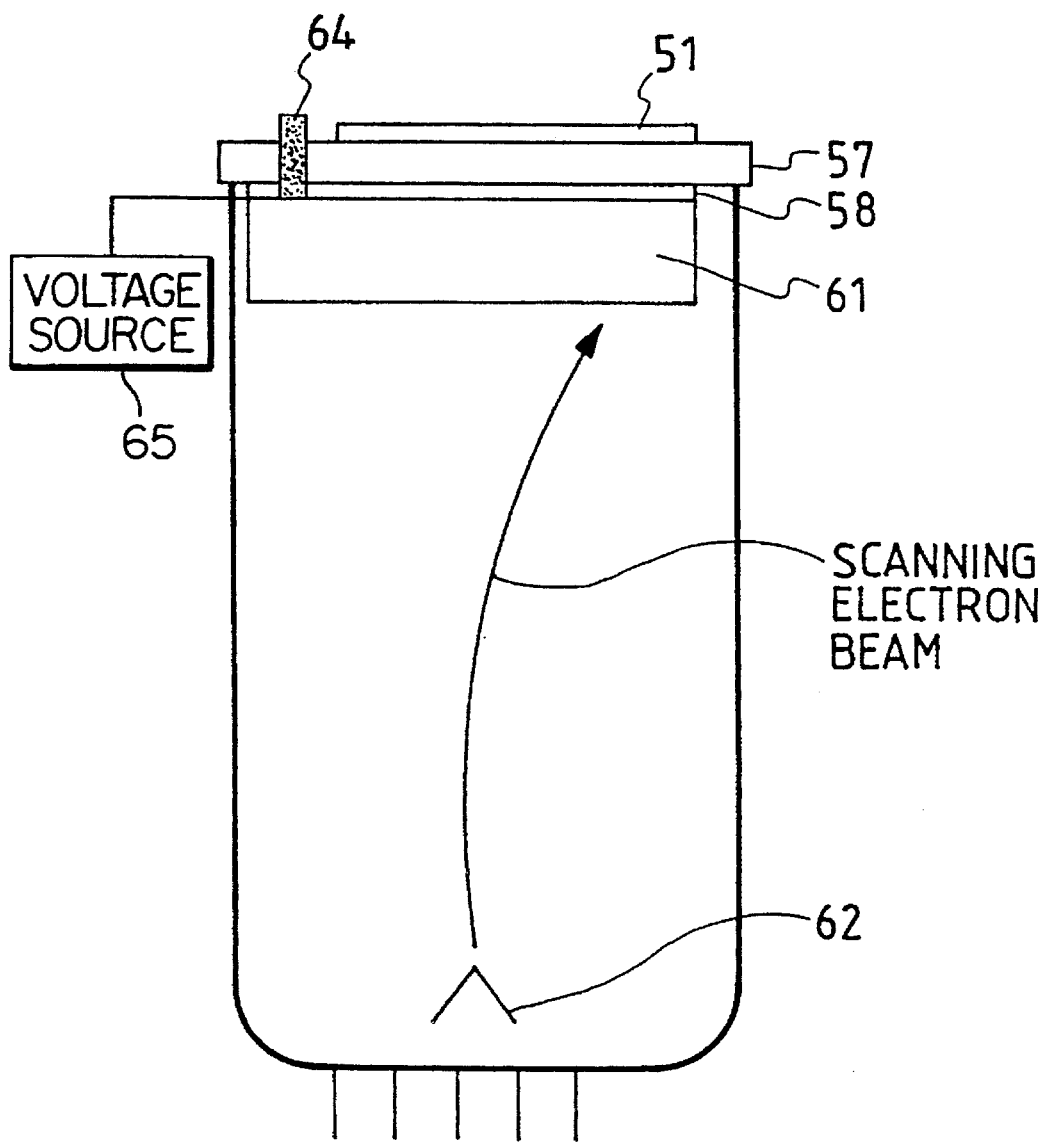
FIG. 13 is an overall elevation view illustrating an example of the avalanche-type imaging device structured as described.

In this embodiment is used the optical lenses 53 in the optical system of the electron detection instrument. To increase the sensitivity further, the transparent substrate of the imaging device should be structured to have the optical fiber plate and the flatting layer laminated together. FIG. 13 depicts an elevation view illustrating an example of the avalanche-type imaging device 54 structured as described above. The example comprises an optical fiber plate 57, a transparent electrode 58, an photoconductive-film 61, a signal pin 64, a cathode 62, and a scintillator 51. The signal light fed out of the scintillator 51 arranged in contact with the optical fiber plate 57 can made to come fully to the photoconductive-film 61 by the optical fiber plate 57 of 100% numerical aperture to generate signal charge. It is desirable to apply a voltage by a voltage source 65 or more particularly a high electric field between the transparent electrode 58 and the cathode 62 through the transparent electrode 58 as to cause avalanche multiplication of charge in the photoconductive-film. This can increase the signal charge generated in the photoconductive-film in an avalanche fashion. The signal charge is read by the scanned electron beam. As a result, a super-high sensitivity characteristic is accomplished together with an effect of the optical fiber plate 57 having little light intensity loss.

Figure 14:
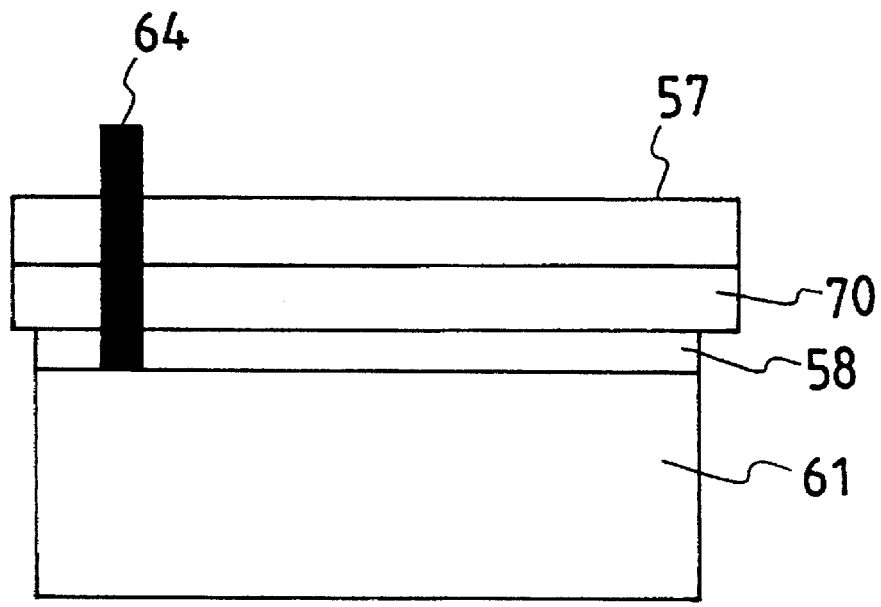
FIG. 14 is an elevation view illustrating an example of eliminating irregularity on a surface of an optical fiber plate according to the present invention.

FIG. 14 depicts an elevation view illustrating an example of eliminating irregularity on the surface of the optical fiber plate 57 by the flatting layer. The example comprises an optical fiber plate 57, a flatting layer 70, a transparent electrode 58, an photoconductive-film 61, and a signal pin 64. The flatting layer 70 should be thinner than at least 10 μm to make it transparent for the visible light and not to cause photon scattering in the flatting layer to deteriorate the resolution. The flatting layer should be prepared in the method given below.

Figure 15:
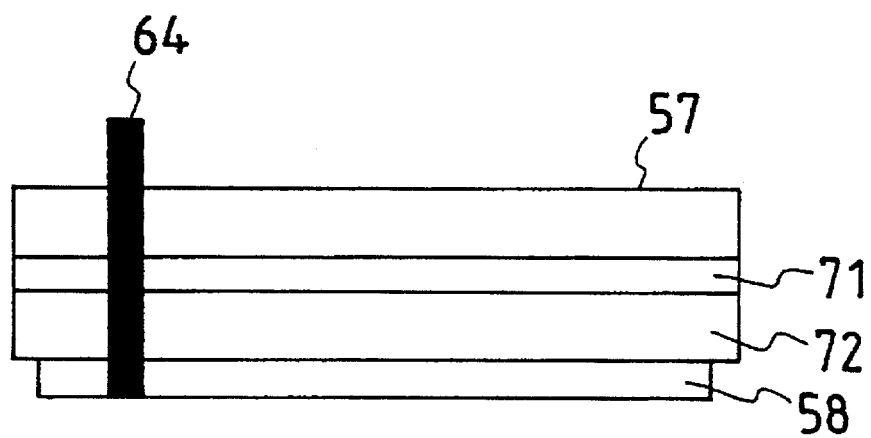
FIG. 15 is an elevation view illustrating an example of process of flatting on the surface of the optical fiber plate.

FIG. 15 depicts an elevation view illustrating an example of process of flatting on the surface of the optical fiber plate 57 according to the present invention. The example comprises the optical fiber plate 57, a bond 71, a thin plate glass 72, the transparent electrode 58, and the signal pin 64. Firstly, the optical fiber plate 57 of one inch diameter should be optically polished in a way similar to ordinary glass polishing. Secondly, the polished optical fiber plate 57 should be bonded with the thin plate glass 72 of 500 μm thick by the bond 71. The bond 71 used was of ultraviolet rays hardening type that has little expansion coefficient when it is solidified. To prevent the bond 71 from absorbing and scattering photons, the bond 71 was made thinner than 1 μm by way of spin painting. After the bond 71 was solidified, the thin plate glass 72 was polished to around 10 μm by way of optical polishing. The thin plate glass 72 was cleaned with an organic solvent. Then, surfaces of the thin plate glass 72 was further dry-etched in an Ar gas atmosphere at 10.6 pascal of partial pressure of Ar to increase the flatness. After that, the thin plate glass 72 was painted with ITO (indium tin oxide) of 0.8 μm thick by sputtering evaporation. The painted thin plate glass 72 was dry-etched in an Ar gas atmosphere like the above again so that the ITO should be around 0.2 μm in the thickness. With the process described above, a surface of the ITO becoming the transparent electrode 58 can be finished to less roughness than 1 nm.

The full process of flatting the optical fiber plate 57 was explained above. If the surface of the thin plate glass 72 is good, sputtering and dry-etching the ITO can be omitted. Just after dry-etching the thin plate glass 72, the ITO may be evaporated onto the transparent electrode 58 to around 100 nm thick. This can complete the flatness.

Figure 16:
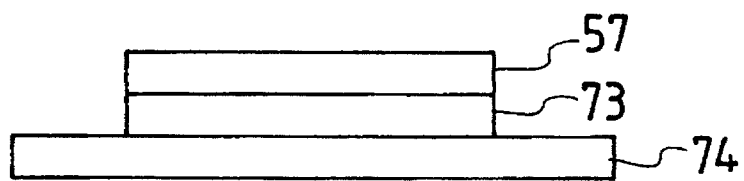
FIG. 16 is flow procedures illustrating another example of process of flatting on the surface of the optical fiber plate.
Figure 16:
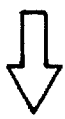
Figure 16:
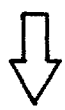
Figure 16:
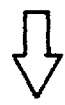
Figure 16:
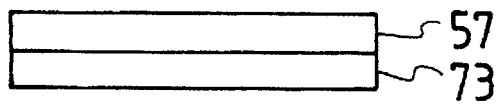
Figure 16:
Figure 16:
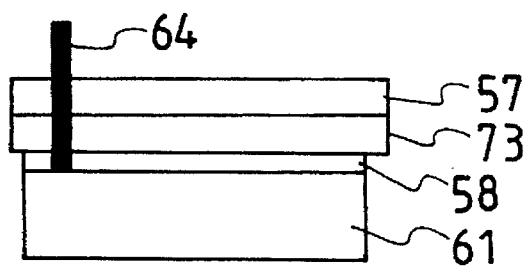

FIG. 16 depicts flow procedures illustrating another example of process of flatting on the surface of the optical fiber plate 58 according to the present invention. The example comprises the optical fiber plate 57, an SOG (spin on glass) 73, and a Si single crystal wafer 74. In the process, firstly, the optical fiber plate 57 of one inch diameter is spin-painted with the SOG 73 on an upper surface thereof to 2 to 3 μm thick by a spinner. Secondly, the Si single crystal wafer 74 and the optical fiber plate 57 are pressed together, with the mirrored surface of the wafer fitted with the SOG. In pressing, they are heat-treated at 450° for 30 min to solidify the SOG. After that, the Si single crystal wafer 74 is optically polished to around 100 μm thick. In turn, the substrate is immersed in a hydrazine solvent to back-etch the Si single crystal wafer 74. The Si single crystal wafer 74 is completely etched in around two hours. The optical fiber plate 57 has a $SiO_2$ surface formed by the heat treatment of the SOG. The $SiO_2$ surface has excellent flatness since the mirrored surface of the Si single crystal wafer 74 is transferred thereto.

On the surface of SOG 73, the transparent electrode 58 is formed as the process shown above (referring FIG. 15), and furthermore the photoconductive-film 61 is formed on this electrode 58.

The first embodiment uses the inorganic SOG. Alternatively, an organic SOG or powder glass can be used to provide equivalent flatness.

In this embodiment, the present invention provides the electron detection instrument for an electron microscope and its manufacturing method. This electron detection instrument has higher sensitivity than prior instruments, and enable to the rapid detection of a weak electron beam such a high-angle scattered electron beam. Thus the electron microscope shown in this embodiment is suitable for 3-dimensional atomic arrangement observation and atomic identification at higher speed.

[EMBODIMENT 3]

Figure 17:
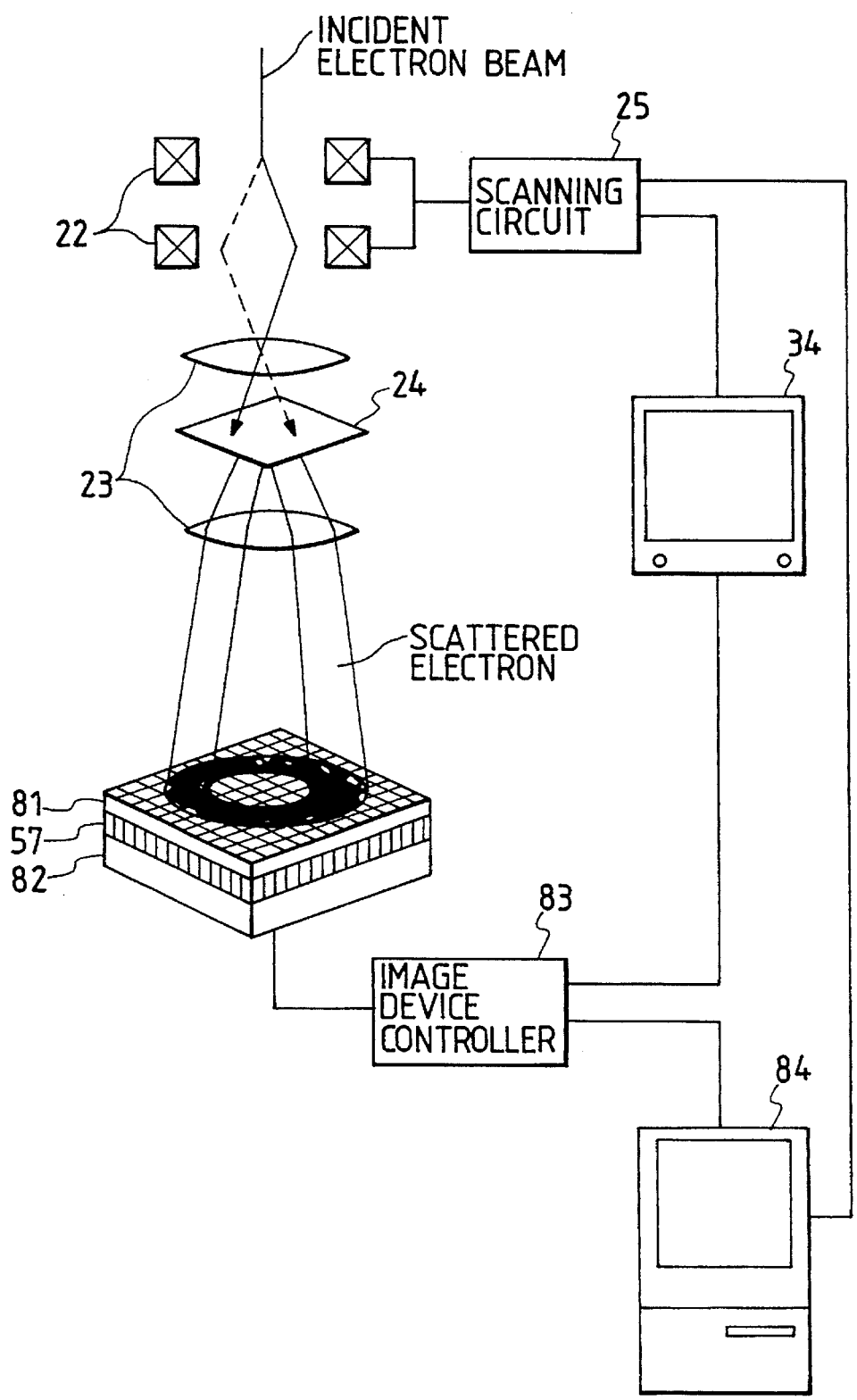
FIG. 17 is an exploded perspective view and a block diagram illustrating an overall configuration of an electron detection instrument for electron microscope used in a second embodiment according to the present invention.

FIG. 17 depicts an exploded perspective view and a block diagram illustrating a basic configuration of an electron detection instrument for electron microscope used in a second embodiment according to the present invention. The electron microscope used in this embodiment (overall structure is not shown in FIG. 17) has almost same structure as the embodiment 1 except for the electron detection instrument. The electron detection instrument comprises a scintillator 81, an optical fiber plate 57, a CCD imaging device 82, an imaging device control system 83, a computer 84, and a monitor 34.

The scintillator has a YAG ($Y_{3-x}Ge_xAl_5O_{12}$) of 550 nm peak luminescence wavelength doped with cerium or GOS ($Gd_2O_2S$) of 510 nm peak luminescence wavelength doped with praseodymium, cerium, or fluorine. The optical fiber plate 57 is used to couple the scintillator 81 with the CCD imaging device 82 optically. The scintillator 81 generates photons isotropically. Numerical aperture of the optical fiber plate 57 is made around 0.6 to 0.8 so that photons directed virtually down can come to the CCD imaging device 82.

This increases a measurement accuracy (angle resolution) and image resolution for the distribution of scattered electron. The CCD imaging device 82 used is a device having more than 1 million pixels. The scintillator 81, the optical fiber plate 57, and the CCD imaging device 82 are positioned to obtain a camera length equivalent to higher maximum detection angle than 200 to 300 mrad for the electrons emitted from a specimen. To detect the refracted electrons, the scintillator 81, the optical fiber plate 57, and the CCD imaging device 82 may be positioned aside or above the specimen.

The imaging device control system 83 controls the input and output of the CCD imaging device 82. The imaging device control system 83 controls at what an address a pixel should be activated among more than 1 million pixels. This allows the CCD pixels to be activated in a circular, annular, or other contours so that the electrons from the specimen can be detected in a desired range of angle. The electron intensity information or image information can be obtained with the signal output of the imaging device control system 83 processed as in the first embodiment. Recording and displaying the information should be made as in the first embodiment.

In this embodiment, the present invention provides the electron microscope using a CCD (charge-coupled device) as an imaging device in the electron detection instrument. Therefore this electron detection instrument has wider dynamic range on intensities of incident electron beams than that of embodiment 2. Thus the electron microscope shown in this embodiment is suitable for atomic identification (especially for trace element analysis) at higher accuracy.

What is claimed is:

1. An electron microscope comprising:

an electron gun;

an electron optic system for illumination;

an electron deflector system;

a specimen holder;

an electron detection instrument including a signal reception section in which a signal detection area detecting signals caused by electrons from the specimen is set arbitrarily; and an electron detection instrument controller controlling said electron detection instrument to scan said signal detection area in said signal reception section thereof corresponding to said electron deflector system.

2. An electron microscope according to claim 1 wherein said signal detection area is scanned concentrically in said signal reception section.

3. An electron microscope according to claim 2, wherein said signal reception section has a multi-channel matrix configuration comprising a plurality of photosensitive devices.

4. An electron microscope according to claim 1, wherein said electron detection instrument comprises a scintillator converting said electrons from the specimen to photons and an imaging device having said signal reception section which detects photons from said scintillator.

5. An electron microscope according to claim 4, wherein said imaging device comprises said signal reception section being a photoconductive-film, means for setting said signal reception section being an electron gun which emits an electron beam toward said photoconductive-film, and means for scanning said signal detection area being electron deflection electrodes which deflect said electron beam.

6. An electron microscope according to claim 4, wherein said imaging device comprises a charge-coupled device.

7. An electron microscope comprising:

an electron gun;

an electron optic system;

a specimen holder;

an electron detection instrument which has a scintillator detecting electrons to convert said electrons detected thereby to photons and an imaging device having a photon reception section; and an imaging device controller which controls said imaging device to set a photodetection area on said photon reception section thereof.

8. An electron microscope according to claim 7, wherein said scintillator has an aluminum film on a surface thereof.

9. An electron microscope according to claim 7, wherein said imaging device is an avalanche-type imaging device.

10. An electron microscope according to claim 7, further comprising:

an optical fiber plate which is arranged between said scintillator and said imaging device.

11. An electron microscope according to claim 7, wherein said imaging device has a multi-channel matrix configuration comprising a plurality of photosensitive devices.

12. An electron microscope according to claim 7, wherein said imaging device comprises a photoconductive-film having said photon reception section on a surface thereof, an electron gun emitting an electron beam toward said surface of said photoconductive-film, and deflection electrodes controlled to scan said electron beam on the surface of said photoconductive-film.

13. An electron microscope according to claim 12, wherein said imaging device has voltage applying means applying a voltage to surfaces of said photoconductive-film.

14. An electron microscope according to claim 13, wherein said voltage applying means applies an electric field substantially $10^6$ V/cm between the surfaces of said photoconductive-film.

15. An electron microscope according to claim 12, wherein said imaging device has an amorphous-selenium photoconductive-film thereof.

16. An electron microscope according to claim 15, wherein said scintillator has the peak luminescence wavelength between 350 and 450 nm thereof.

17. An electron microscope according to claim 15, wherein said scintillator consists of metal oxo silicate doped with cerium.

18. An electron microscope according to claim 17, wherein said metal oxo silicate is selected from the group consisting of gadolinium oxo silicate ($Gd_2SiO_5$), yttrium oxo silicate ($Y_2SiO_5$), and lutetium oxo silicate ($Lu_2SiO_5$).

19. An electron detection instrument for an electron microscope comprising:

a scintillator converting electrons detected thereby to photons; and an imaging device having a photon reception section on which a photondetection area detecting said photons from said scintillator is set arbitrarily.

20. An electron detection instrument for an electron microscope according to claim 19, wherein said scintillator has an aluminum film on a surface thereof.

21. An electron detection instrument for an electron microscope according to claim 19, further comprising:

an optical fiber plate which is arranged between said scintillator and said imaging device.

22. An electron detection instrument for an electron microscope according to claim 19, wherein said imaging device comprises a photoconductive-film having said photon reception section on a surface thereof, and means for setting said photondetection area detecting photons from said scintillator in said photon reception section of the photoconductive-film.

23. An electron detection instrument for an electron microscope according to claim 22, wherein said means for setting said photondetection area comprises an electron gun emitting an electron beam toward said surface of said photoconductive-film, and deflection electrodes scanning said electron beam on said surface of the photoconductive-film.

24. An electron detection instrument for an electron microscope according to claim 22, wherein said photoconductive-film has a transparent electrode on a surface thereof.

25. An electron detection instrument for an electron microscope according to claim 22, wherein said imaging device has an amorphous-selenium photoconductive-film thereof.

26. An electron detection instrument for an electron microscope according to claim 22, wherein said scintillator has the peak luminescence wavelength between 350 and 450 nm thereof.

27. An electron detection instrument for an electron microscope according to claim 22, wherein said scintillator consists of metal oxo silicate doped with cerium.

28. An electron detection instrument for an electron microscope according to claim 27, wherein said metal oxo silicate is selected from the group consisting of gadolinium oxo silicate ($Gd_2SiO_5$), yttrium oxo silicate ($Y_2SiO_5$), and lutetium oxo silicate ($LU_2SiO_5$).

* * * * *

UNITED STATES PATENT AND TRADEMARK OFFICE
Certificate

Patent No. 5,552,602            Patented: September 3, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Hiroshi Kakibayashi, Yasuhiro Mitsui, Hideo Todokoro, Katsuhiro Kuroda, Masanari Koguchi, Kazutaka Tsuji, Tatsuo Makishima, Mikio Ichihashi, and Shigeto Isakozawa.

Signed and Sealed this Third Day of November, 1998.

EDWARD P. WESTIN
                                             *Supervisory Patent Examiner*
                                                   Group Art Unit 2878